US00PP08609P

United States Patent [19]

VandenBerg

[11] Patent Number: Plant 8,609

[45] Date of Patent: Feb. 22, 1994

[54] CHRYSANTHEMUM PLANT NAMED TRACY

[75] Inventor: Cornelis P. VandenBerg, Salinas, Calif.

[73] Assignee: Yoder Brothers, Inc., Barberton, Ohio

[21] Appl. No.: 986,518

[22] Filed: Dec. 7, 1992

[51] Int. Cl.[5] ..... A01H 5/00

[52] U.S. Cl. ..... Plt./82.1

[58] Field of Search ..... Plt. 82.1

*Primary Examiner*—Howard J. Locker

*Attorney, Agent, or Firm*—Foley & Lardner

[57] ABSTRACT

A Chrysanthemum plant named Tracy particularly characterized by its flat capitulum form; duplex daisy capitulum type; white ray floret color; diameter across face of capitulum of 54 to 70 mm when fully opened; branching pattern is spreading and prolific, with 7 to 9 breaks after pinch when grown outside under natural daylength in fall flowerings and with 5 to 7 breaks after pinch in 10 cm pots for spring flowerings; natural season flower date of Aug. 27 to 29 when planting rooted cuttings on Jun. 21 to 23 in Salinas, Calif., and Sep. 23 to 28 when planting rooted cuttings Jun. 15 to Jun. 18 in Hightstown, N.J.; flowering response of 48 to 56 days after rooting in no light/no shade programs in spring in Salinas, Calif.; plant height of 20 to 33 cm when grown in fall under natural daylength with no growth regulators in New Jersey, and 13 to 18 cm when grown in 10 cm pots in spring with 0 to 2 applications of 2500 ppm B-9 SP; and durable, uniform performance.

3 Drawing Sheets

The present invention comprises a new and distinct cultivar of Chrysanthemum, botanically known as *Dendranthema grandiflora*, and referrred to by the cultivar name Tracy.

Tracy, identified as 8259 (85-092001) was originated from a cross made by Cornelis P. VandenBerg in a controlled breeding program in Salinas, Calif., in 1985.

The female parent of Tracy was an unnamed seedling identified as 2625 (82-M49004), and described as a white decorative garden mum having a flower diameter of 64 to 76 mm, a natural season flower date of Aug. 24 to 27 in Salinas, Calif., and Sep. 26 to 30 in Hightstown, N.J., a flowering response in spring of 48 to 54 days, and a plant height of 25 to 28 cm in fall natural season flowerings in New Jersey, and 20 to 23 cm in spring flowerings in 10 cm pots with no growth regulator in Salinas, Calif. The female parent of Tracy was discarded from the program in Oct. 1987.

The male parent of Tracy was the cultivar identified as Allure, disclosed in U.S. Plant Pat. No. 5,989, and described as a yellow daisy garden mum, having a flower diameter of 51 to 70 mm, a natural season flower date of Aug. 21 to 26 in Salinas, Calif., and Sep. 26 to 27 in Hightstown, N.J., and a plant height of 23 to 33 cm in fall natural season flowerings in New Jersey, and 18 to 25 cm in spring flowerings in 10 cm pots with no growth regulator in Salinas.

Tracy was discovered and selected as one flowering plant within the progeny of the stated cross by Cornelis P. VandenBerg in Sep. 1986, in a controlled environment in Salinas, Calif.

The first act of asexual reproduction of Tracy was accomplished when vegetative cuttings were taken from the initial selection in Nov. 1986 in a controlled environment in Salinas, Calif., by technicians working under supervision of Cornelis P. VandenBerg.

Horticultural examination of controlled flowerings of successive plantings has shown that the unique combination of characteristics as herein disclosed for Tracy are firmly fixed and are retained through successive generations of asexual reproduction.

Tracy has not been observed under all possible environmental conditions. The phenotype may vary significantly with variations in environment such as temperature, light intensity and daylength, without, however, any variance in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during Jun. through Oct. Spring flowerings were conducted in Salinas, Calif. under geenhouse conditions which approximate those generally used in commercial practice for small pot spring garden mum production.

The following traits have been repeatedly observed and are determined to be basic characteristics of Tracy, which, in combination, distinguish this Chrysanthemum as a new and distinct cultivar:

1. Flat capitulum form.
2. Daisy capitulum type, with 4 to 6 layers of ray florets.
3. White ray floret color.
4. Diameter across face of capitulum of 54 to 70 mm when fully opened.
5. Branching pattern is spreading and prolific, with 7 to 9 breaks after pinch when grown outside under natural daylength in fall flowerings and with 5 to 7 breaks after pinch in 10 cm pots for spring flowerings.
6. Natural season flower date of Aug. 27 to 29 when planting rooted cuttings on Jun. 21 to 23 in Salinas, Calif., and Sep. 23 to 28 when planting rooted cuttings Jun. 15 to 18 in Hightstown, N.J.
7. Flowering response of 48 to 56 days after rooting in no light/no shade programs in spring in Salinas, Calif.
8. Plant height of 20 to 33 cm when grown in fall under natural daylength with no growth regulators in New Jersey, and 13 to 18 cm when grown in 10 cm pots in spring with 0 to 2 applications of 2500 ppm B-9 SP.
9. Durable, uniform performance.

The accompanying photographic drawings show typical inflorescence and leaf characteristics of Tracy, with the colors being as nearly true as possible with illustrations of this type.

Sheet 1 is a color photograph of Tracy grown as a pinched garden pot mum under natural season conditions outside in Salinas, Calif.

Sheet 2 is a black and white photograph of three views of the inflorescence of Tracy.

Sheet 3 is a black and white photograph showing the upper and under sides of the leaves of Tracy at 3 stages of development (mature, intermediate and immature). In sheets 2 and 3 a measuring tape in centimeters has been added.

Of the commercial cultivars known to the inventor, the most similar in comparison to Tracy is the cultivar identified as White Stardom, disclosed in U.S. Plant Pat. No. 3,999. Reference is made to attached Chart A, which compares certain characteristics of Tracy to the same characteristics of White Stardom.

Similar traits are ray floret color, capitulum form and type, branching pattern, natural season flowering response in Salinas, Calif. and controlled flowering response in spring flowering in Salinas, Calif. Tracy has a faster flowering response in New Jersey and generally a shorter plant height in natural season fall flowering when compared with White Stardom. In addition, plants of White Stardom frequently die because of root loss in wet locations. This problem has not been observed in Tracy. In production of vegetative cuttings White Stardom shows many problems because of early budding. This problem has not been observed in Tracy.

In the following description color references are made to The Royal Horticultural Society Colour Chart. The color values were determined on plant material grown as a pinched garden mum under natural conditions outside in Salinas, Calif. on Aug. 20, 1992.

Classification:

*Botanical.*—*Dendranthema grandiflora* cv Tracy.

*Commercial.*—Flat daisy spray pot mum and garden mum.

INFLORESCENCE

A. Capitulum:

*Form.*—Flat.

*Type.*—Daisy with 4 to 6 layers of ray florets.

*Diameter across face.*—54 to 70 mm when fully opened.

B. *Corolla of ray florets:*

*Color (general tonality from a distance of three meters).*—White.

*Color (upper surface).*—155D, maturing to clear white.

*Color (under surface).*—155D.

*Shape.*—Cross-section concave, longitudinal section of outer ray florets slightly convex.

C. Corolla of disc florets:

*Color (mature).*—14B.

*Color (immature).*—14B.

D. Reproductive organs:

*Androecium.*—Present on disc florets only; moderate pollen.

*Gynoecium.*—Present on both ray and disc florets.

PLANT

A. General appearance:

*Height.*—20 to 33 cm when grown in fall under natural daylength in New Jersey with no growth regulators, and 18 to 23 cm when grown in 10 cm pots in spring in Salinas, Calif. with 0 to 2 applications of 2500 ppm B-9 SP.

*Branching pattern.*—Spreading and prolific, with 7 to 9 breaks after pinch when grown outside under natural daylength in fall flowerings, and 5 to 7 breaks after pinch in 10 cm pots for spring flowerings.

B. Foliage:

*Color (upper surface).*—147A.

*Color (under surface).*—147B.

*Shape.*—See photograph.

CHART A

| CULTIVAR | TRACY | WHITE STARDOM |
|---|---|---|
| Ray floret color | White | White |
| Capitulum form and type | Flat Daisy | Flat Daisy |
| Diameter across face of capitulum | 54 to 70 mm | 57 to 64 mm |
| Branching pattern | Spreading and prolific | Spreading and prolific |
| Nat. season flower date: | | |
| in Salinas, CA | Aug 27 to 29 | Aug 25 to 31 |
| in Hightstown, NJ | Sep 23 to 28 | Sep 28 to Oct 3 |
| Controlled response | 48 to 56 days | 47 to 56 days |
| Plant height: | | |
| in natural season fall | 20 to 33 cm | 30 to 36 cm |
| in 10 cm pots spring | 18 to 23 cm | 18 to 30 cm |

COMPARISONS MADE OF PLANTS GROWN UNDER NATURAL SEASON OUTDOOR CONDITIONS IN SALINAS, CALIFORNIA AND IN HIGHTSTOWN, NEW JERSEY AND IN SPRING FLOWERING PROGRAMS IN SALINAS, CALIFORNIA

I claim:

1. A new and distinct Chrysanthemum plant named Tracy, as described and illustrated.

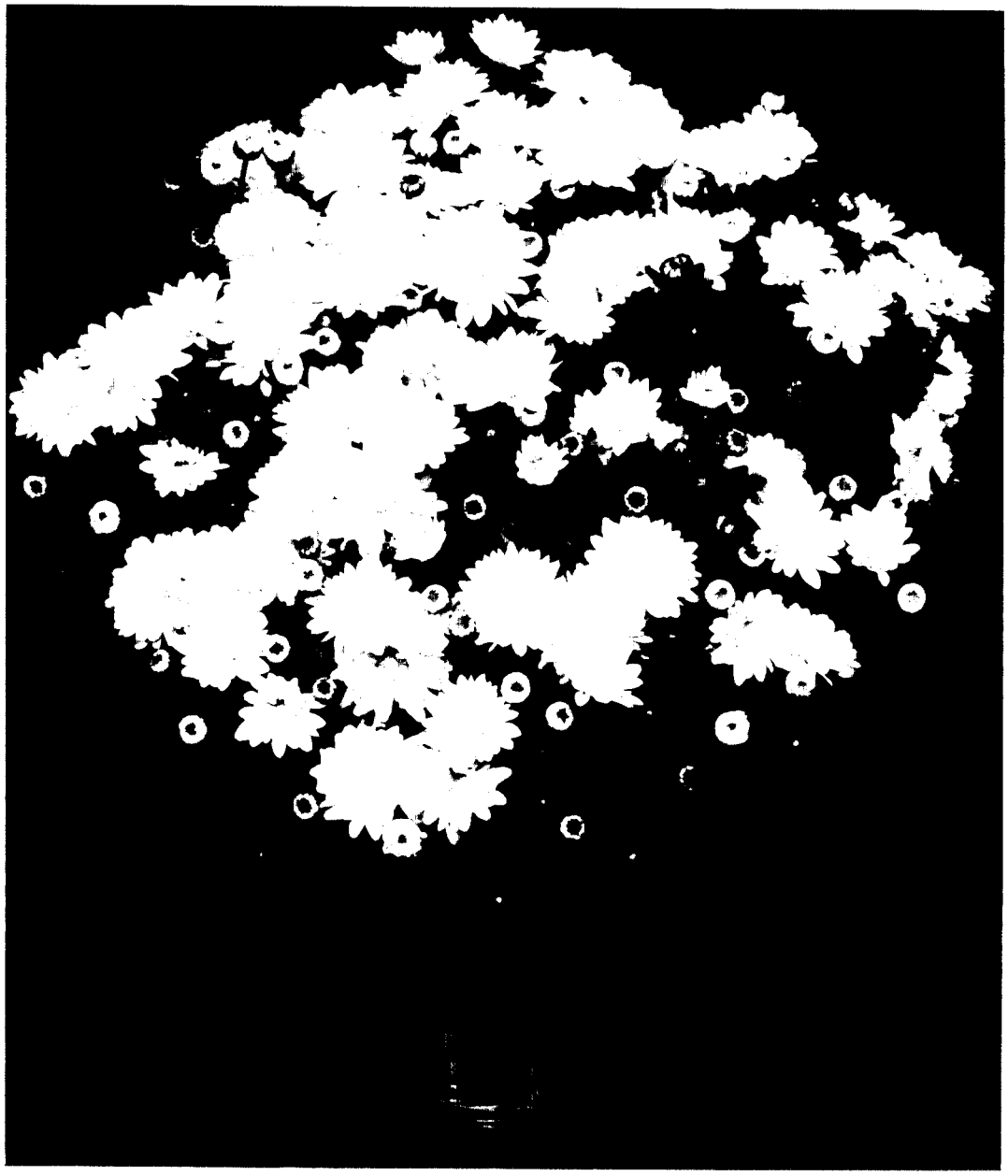

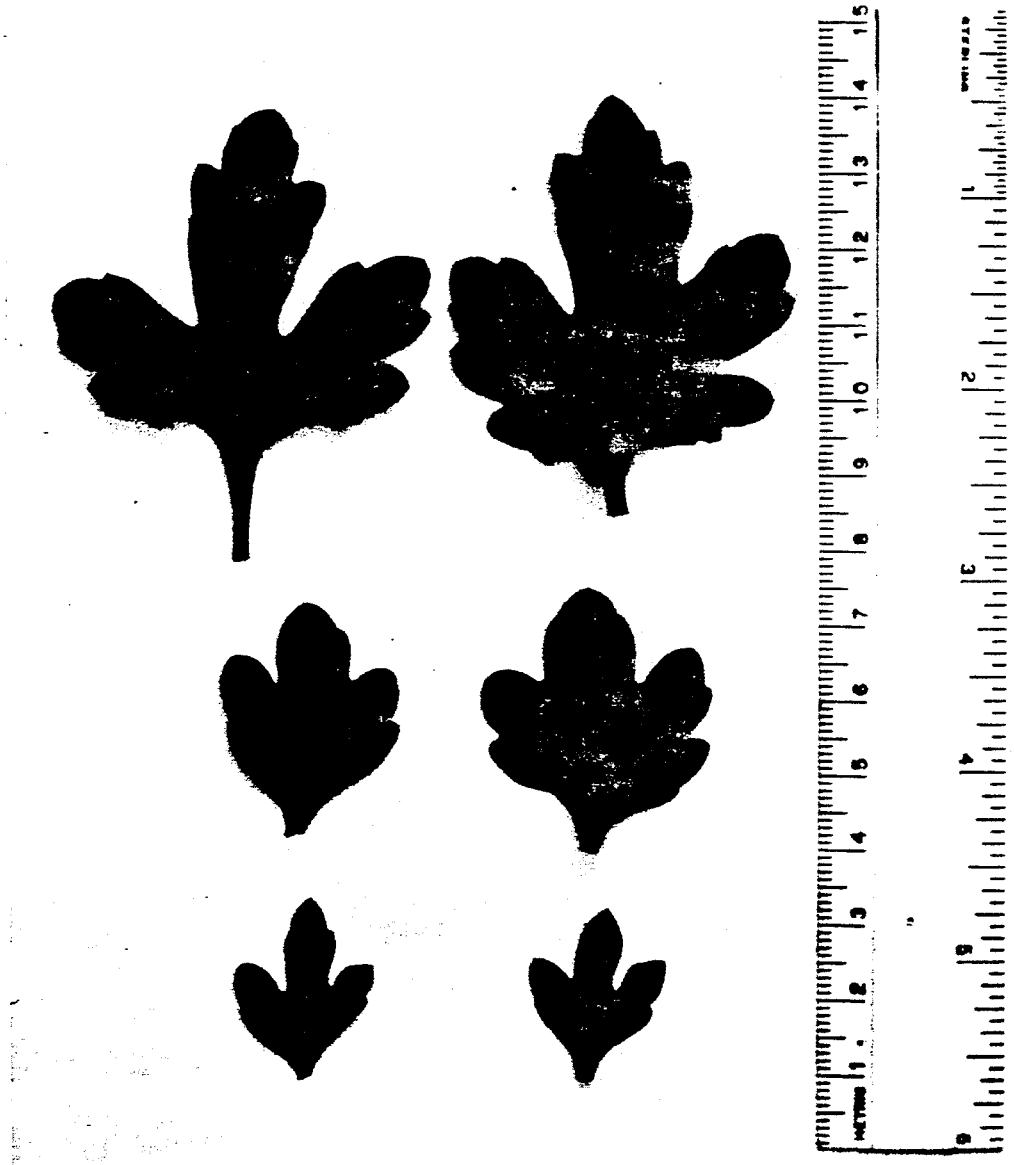

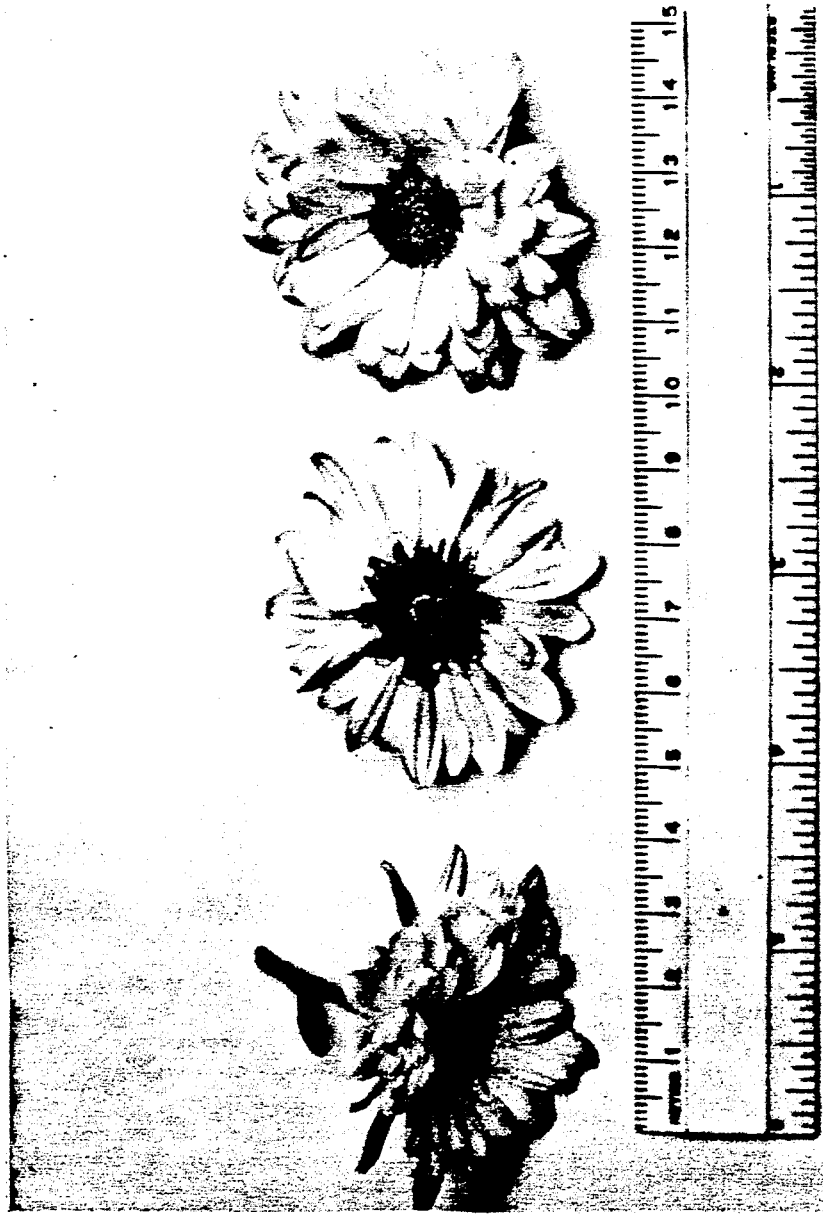

* * * * *